(12) United States Patent
Ishikawa et al.

(10) Patent No.: US 9,453,800 B2
(45) Date of Patent: Sep. 27, 2016

(54) APPARATUS AND METHOD OF INSPECTING A DEFECT OF AN OBJECT

(71) Applicant: Samsung Electronics Co., Ltd., Suwon-si (KR)

(72) Inventors: Akio Ishikawa, Yokohama (JP); Mitsuhiro Togashi, Yokohama (JP); Mitsunori Numata, Yokohama (JP)

(73) Assignee: Samsung Electronics Co., Ltd. (KR)

( * ) Notice: Subject to any disclaimer, the term of this patent is extended or adjusted under 35 U.S.C. 154(b) by 359 days.

(21) Appl. No.: 14/142,093

(22) Filed: Dec. 27, 2013

(65) Prior Publication Data

US 2014/0185044 A1 Jul. 3, 2014

(30) Foreign Application Priority Data

Dec. 27, 2012 (JP) .............................. 10-2012-286202

(51) Int. Cl.
| | |
|---|---|
| *G01N 21/21* | (2006.01) |
| *G01N 21/95* | (2006.01) |
| *G01N 21/88* | (2006.01) |
| *G01N 21/956* | (2006.01) |

(52) U.S. Cl.
CPC ........ *G01N 21/8806* (2013.01); *G01N 21/956* (2013.01); *G01N 21/21* (2013.01); *G01N 21/95607* (2013.01); *G01N 21/95623* (2013.01); *G01N 2021/8825* (2013.01); *G01N 2021/8848* (2013.01)

(58) Field of Classification Search
USPC .............. 356/237.1–241.6, 242.1–243.8, 356/426–431, 600–640, 445–448, 450–458
See application file for complete search history.

(56) References Cited

U.S. PATENT DOCUMENTS

| | | | | |
|---|---|---|---|---|
| 3,630,598 A | * | 12/1971 | Little, Jr. ........... | G02B 27/4238 359/3 |
| 4,351,589 A | * | 9/1982 | Chavel ..................... | G06E 1/04 349/17 |
| 4,943,151 A | * | 7/1990 | Cushman ................. | A61B 3/09 351/203 |
| 5,046,847 A | * | 9/1991 | Nakata .................... | G01N 21/94 250/559.41 |
| 5,673,103 A | * | 9/1997 | Inoue .................. | G03F 7/70058 355/53 |
| 5,684,851 A | * | 11/1997 | Kurbatov ............. | G01N 23/046 378/149 |
| 5,695,268 A | * | 12/1997 | Hagiwara ................. | F21V 9/14 349/9 |
| 5,717,733 A | * | 2/1998 | Kurbatov ............. | G01N 23/207 378/2 |
| 6,239,873 B1 | * | 5/2001 | Videen ................... | G01N 21/21 356/369 |
| 6,639,673 B1 | * | 10/2003 | Freund ................. | G01B 11/065 356/369 |
| 7,173,956 B2 | * | 2/2007 | Palese ................... | G02F 1/0311 372/92 |
| 7,345,754 B1 | * | 3/2008 | Zhao .................. | G01N 21/4738 356/237.1 |
| 7,711,216 B2 | * | 5/2010 | Lewis .................. | G02B 6/1345 385/11 |
| 8,351,033 B2 | * | 1/2013 | Katsunuma ........ | G02B 27/0018 356/327 |
| 8,723,118 B2 | * | 5/2014 | McEldowney ........... | G01J 3/02 250/226 |
| 2005/0046830 A1 | * | 3/2005 | Karp ....................... | G01N 21/21 356/237.1 |
| 2006/0146404 A1 | * | 7/2006 | Ioki ................... | G02F 1/133308 359/484.01 |
| 2014/0055737 A1 | * | 2/2014 | Finley ...................... | G02C 7/12 351/49 |
| 2014/0253790 A1 | * | 9/2014 | Matherson ......... | H04N 1/02805 348/361 |

\* cited by examiner

*Primary Examiner* — Tri Ton
*Assistant Examiner* — Jarreas C Underwood
(74) *Attorney, Agent, or Firm* — Myers Bigel & Sibley, P.A.

(57) ABSTRACT

An apparatus for detecting a defect of an object may include a light emitter configured to emit straight polarized lights having different polarized directions, a spatial filter having openings through which the straight polarized lights selectively pass, an optical member configured to condense the straight polarized lights, which pass through the openings, on the object, and a light detector configured to detect lights reflected from the object. Thus, the defect may be accurately detected in a short time.

16 Claims, 16 Drawing Sheets

FIG. 4A
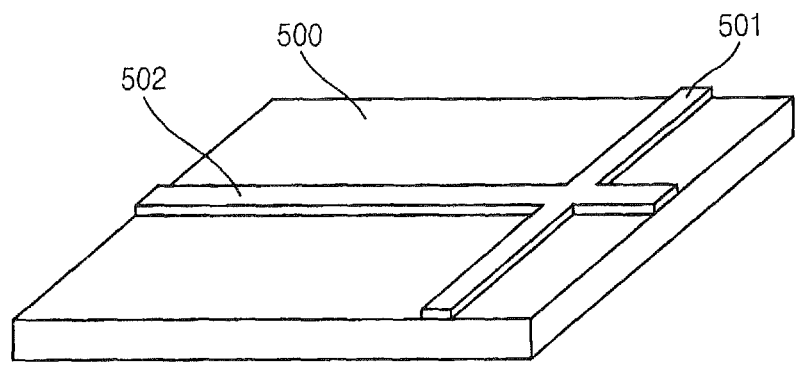
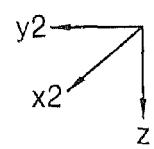
FIG. 4B
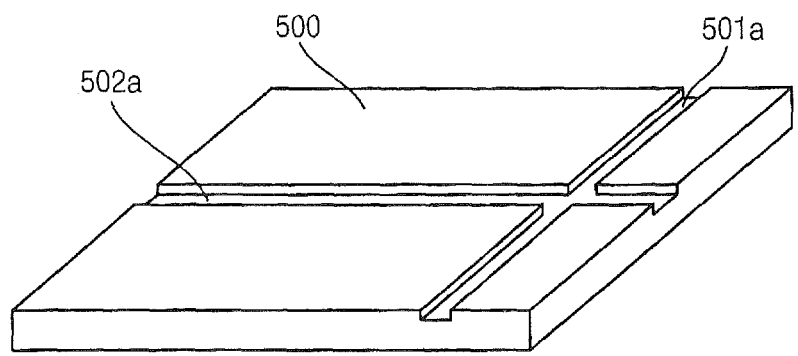
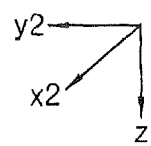

APPARATUS AND METHOD OF INSPECTING A DEFECT OF AN OBJECT

CROSS-RELATED APPLICATION

This application claims priority under 35 USC §119 to Japanese Patent Application No. 2012-286202, filed on Dec. 27, 2012 in the Japanese Intellectual Property Office, the contents of which are herein incorporated by reference in their entirety.

BACKGROUND

1. Field

Example embodiments relate to an apparatus and a method of inspecting a defect of an object.

2. Description of the Related Art

A semiconductor device may be tested using various defect detection methods. The defect detection methods may use a bright field image, a dark field image, a scattering, etc.

As the semiconductor device may have been highly integrated, a defect, such as a foreign substance in a minute pattern of the semiconductor device, may be only several nanometers in size. Thus, it may be difficult to accurately detect the minute defect.

U.S. Pat. No. 7,345,754 may disclose a method of detecting a defect using a light partially blocked by a spatial filter. The method may detect the defect on a pattern having a specific directivity using light partially blocked by the spatial filter.

When light that is partially blocked by the spatial filter is used, only defect detection with respect to the pattern having the specific directivity may be improved. Thus, when a defect in a pattern has a directivity different from the specific directivity that can be detected, it may be required to change an illumination direction of the light in accordance with the different directivity so that a time for detecting the defect in the pattern may be too long.

SUMMARY

Example embodiments provide an apparatus and a method of detecting a defect of an object that may be capable of detecting in a short time.

According to example embodiments, there may be provided an apparatus for detecting a defect of an object. The apparatus may include a light emitter configured to emit straight polarized lights having different polarized directions, a spatial filter having openings through which the straight polarized lights selectively pass, an optical member configured to condense the straight polarized lights, which pass through the openings, on the object, and a light detector configured to detect lights reflected from the object.

In example embodiments, the light emitter may include a light source configured to emit a non-polarized light, and a polarizing filter configured to convert the non-polarized light into the straight polarized lights.

In example embodiments, the polarizing filter may be configured to provide the straight polarized lights with perpendicular polarizing directions.

In example embodiments, the polarizing filter may be integrally formed with the spatial filter.

In example embodiments, the polarizing filter and the spatial filter may have first openings and second openings located at different directions. A first polarizing portion configured to polarize the straight polarized lights in a first direction may be arranged in the first opening. A second polarizing portion configured to polarize the straight polarized lights in a second direction different from the first direction may be arranged in the second opening.

In example embodiments, the first direction may be substantially perpendicular to the direction of the first opening. The second direction may be substantially perpendicular to the direction of the second opening.

In example embodiments, the direction of the first opening may be substantially perpendicular to the direction of the second opening.

In example embodiments, the light emitter may include a plurality of lights sources configured to separately emit the straight polarized lights.

In example embodiments, wherein the openings of the spatial filter may correspond to the straight polarized lights. The openings of the spatial filter may be located at ends of a direction substantially perpendicular to the polarized directions.

In example embodiments, the light detector may include a plurality of light detectors. The light detectors may include a dividing member configured to divide the reflected lights into polarized lights. The light detectors may individually detect the polarized lights.

In example embodiments, the light detectors may include two kinds of the lights detectors. The polarized lights may be substantially perpendicular to each other.

In example embodiments, the dividing member may include a splitter.

In example embodiments, the dividing member may include a reflecting mirror configured to divide the reflected lights into a plurality of light fluxes, and a plurality of polarizing filters configured to provide the divided light fluxes with different polarized directions.

In example embodiments, the reflecting mirror may be configured to divide the reflected lights into the two light fluxes. The spatial filters may be configured to provide the two light fluxes with perpendicular polarized directions.

In example embodiments, the apparatus further include a regular reflection cut filter arranged at a rear optical axis of the condenser lens to cut regularly reflected lights in the reflected lights.

In example embodiments, the apparatus may further include a ½ wavelength plate arranged at any one of an optical axis between the condenser lens and the spatial filter and a rear optical axis of the condenser lens.

According to example embodiments, there may be provided a method of detecting a defect of an object. In the method of detecting the defect of the object, straight polarized lights having different polarized directions may be emitted. The straight polarized lights may be partially cut using openings of a spatial filter. The straight polarized lights passing through the openings may be condensed on the object. Lights reflected from the object may be detected.

According to example embodiments, the defect may be accurately detected in a short time.

BRIEF DESCRIPTION OF THE DRAWINGS

Example embodiments will be more clearly understood from the following detailed description taken in conjunction with the accompanying drawings. FIGS. 1 to 14 represent non-limiting, example embodiments as described herein.

FIG. 1 is a block diagram illustrating an apparatus for detecting a defect of an object in accordance with example embodiments;

FIG. 2 is a schematic view illustrating a measuring unit of the apparatus in FIG. 1;

FIGS. 4A and 4B are perspective views illustrating objects in FIG. 1;

FIG. 5 is a flow chart illustrating a method of detecting a defect of an object using the apparatus in FIG. 1;

FIG. 6 is a schematic view illustrating a measuring unit in accordance with example embodiments;

FIG. 9 is a schematic view illustrating relations between an incident direction, a polarized direction and an object in accordance with example embodiments;

FIG. 10 is a graph showing signal intensities by comparative examples;

FIG. 11 is a schematic view illustrating a measuring unit in accordance with example embodiments;

FIG. 12 is a cross-sectional view illustrating a total reflection cut filter in accordance with example embodiments;

FIG. 13 is a cross-sectional view illustrating a measuring unit in accordance with example embodiments; and FIG. 14 is a cross-sectional view illustrating a measuring unit in accordance with example embodiments.

DETAILED DESCRIPTION OF THE EMBODIMENTS

Figure 1:
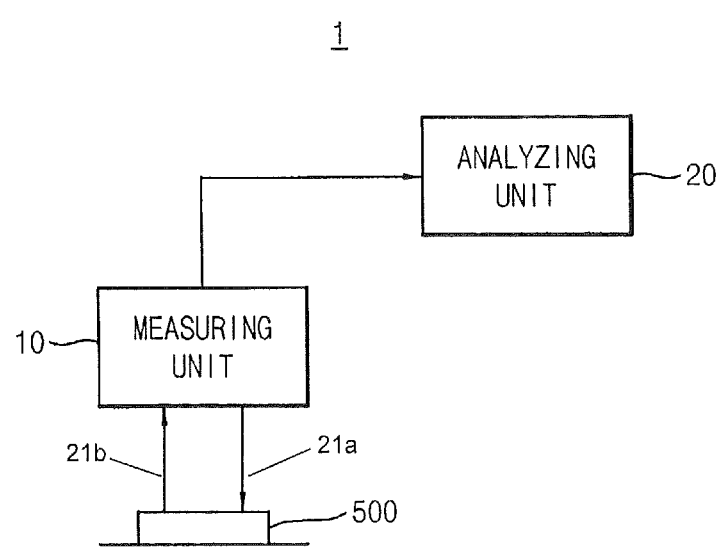

Various example embodiments will be described more fully hereinafter with reference to the accompanying drawings, in which some example embodiments are shown. The present invention may, however, be embodied in many different forms and should not be construed as limited to the example embodiments set forth herein. Rather, these example embodiments are provided so that this disclosure will be thorough and complete, and will fully convey the scope of the present invention to those skilled in the art. In the drawings, the sizes and relative sizes of layers and regions may be exaggerated for clarity.

It will be understood that when an element or layer is referred to as being "on," "connected to" or "coupled to" another element or layer, it can be directly on, connected or coupled to the other element or layer or intervening elements or layers may be present. In contrast, when an element is referred to as being "directly on," "directly connected to" or "directly coupled to" another element or layer, there are no intervening elements or layers present. Like numerals refer to like elements throughout. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

Spatially relative terms, such as "beneath," "below," "lower," "above," "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The terminology used herein is for the purpose of describing particular example embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Example embodiments are described herein with reference to cross-sectional illustrations that are schematic illustrations of idealized example embodiments (and intermediate structures). As such, variations from the shapes of the illustrations as a result, for example, of manufacturing techniques and/or tolerances, are to be expected. Thus, example embodiments should not be construed as limited to the particular shapes of regions illustrated herein but are to include deviations in shapes that result, for example, from manufacturing. For example, an implanted region illustrated as a rectangle will, typically, have rounded or curved features and/or a gradient of implant concentration at its edges rather than a binary change from implanted to non-implanted region. Likewise, a buried region formed by implantation may result in some implantation in the region between the buried region and the surface through which the implantation takes place. Thus, the regions illustrated in the figures are schematic in nature and their shapes are not intended to illustrate the actual shape of a region of a device and are not intended to limit the scope of the present invention.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, example embodiments will be explained in detail with reference to the accompanying drawings.

FIG. 1 is a block diagram illustrating an apparatus for detecting a defect of an object in accordance with example embodiments.

Referring to FIG. 1, an apparatus 1 for detecting a defect of an object 500 may include a measuring unit 10 and analyzing unit 20. The measuring unit 10 may irradiate light 21a onto the object 500. A surface of the object 500 may be scanned by the light. The measuring unit 10 may detect light 21b reflected from the surface of the object 500. The measuring unit 10 may generate an image of the surface of the object 500 based on signal intensities of the reflected light 21b. The analyzing unit 20 may compare the image with a reference image to obtain a difference between the image and the reference image. The analyzing unit 20 may detect the defect based on the difference between the image and the reference image.

Figure 2:
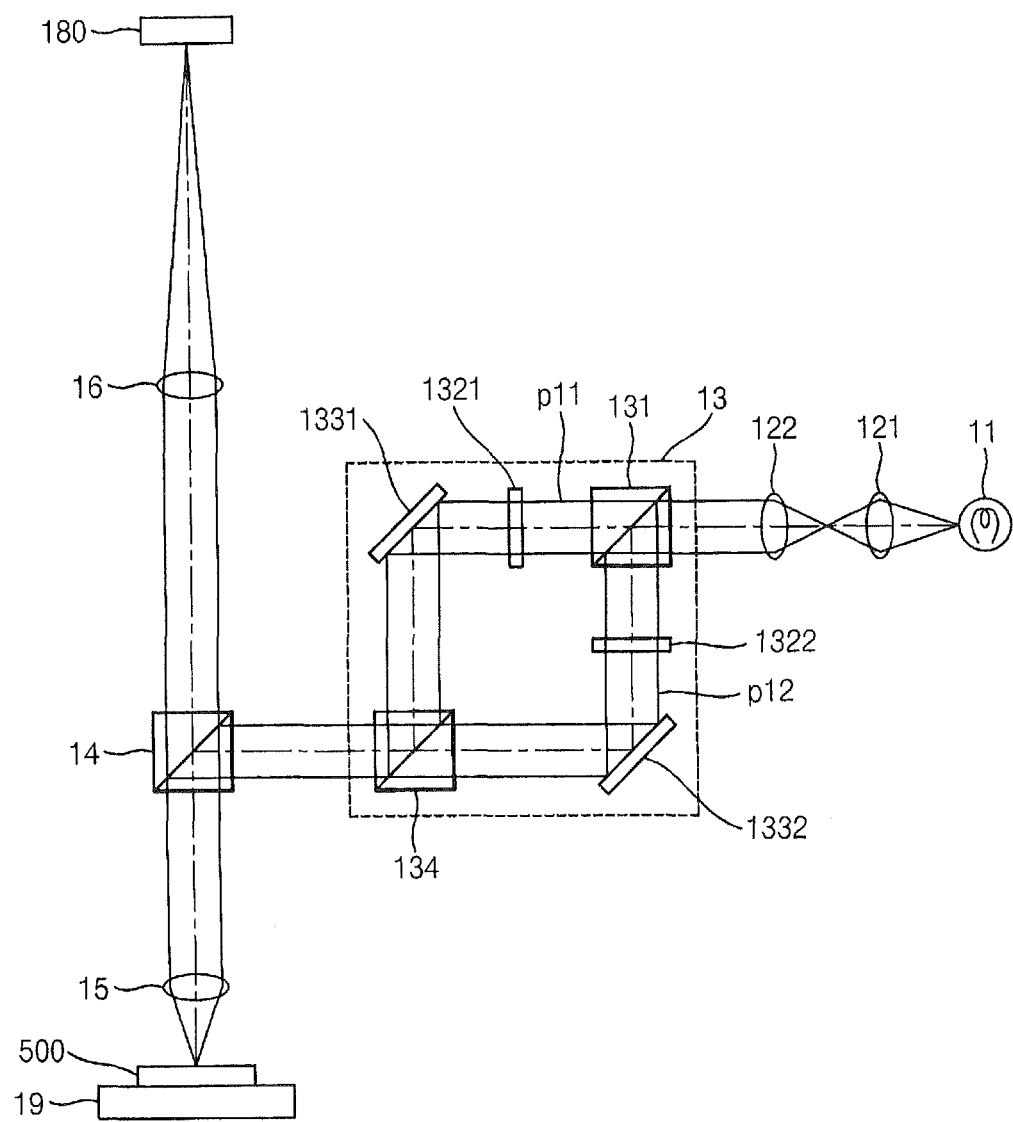

FIG. 2 is a schematic view illustrating a measuring unit of the apparatus in FIG. 1.

Referring to FIG. 2, the measuring unit 10 may include a light source 11, a filter unit 13, relay lenses 121 and 122, a non-polarizing beam splitter (NBS) 14, a condenser lens 15, an imaging lens 16 and a light detector 180. The filter unit 13 may include polarizing beam splitters (PBS) 131 and 134, spatial filters 1321 and 1322 and total reflection mirrors 1331 and 1332.

The light source 11 may emit a non-polarized light. The light emitted from the light source 11 may be converted into a parallel beam by the relay lenses 121 and 122. The parallel beam may be guided to the PBS 131. The PBS 131 may divide the parallel beam into straight polarized beams p11 and p12 that are substantially perpendicular to each other. The straight polarized beam p11 may be guided to the spatial filter 1321. The straight polarized beam p12 may be guided to the spatial filter 1322.

Figure 3A:
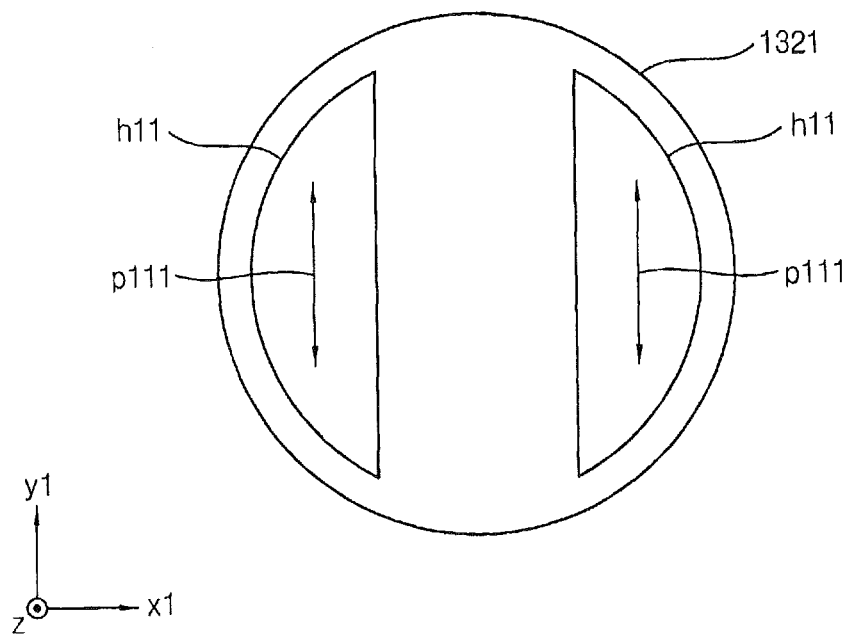
FIGS. 3A and 3B are cross-sectional views illustrating spatial filters of the apparatus in FIG. 1.
Figure 3B:
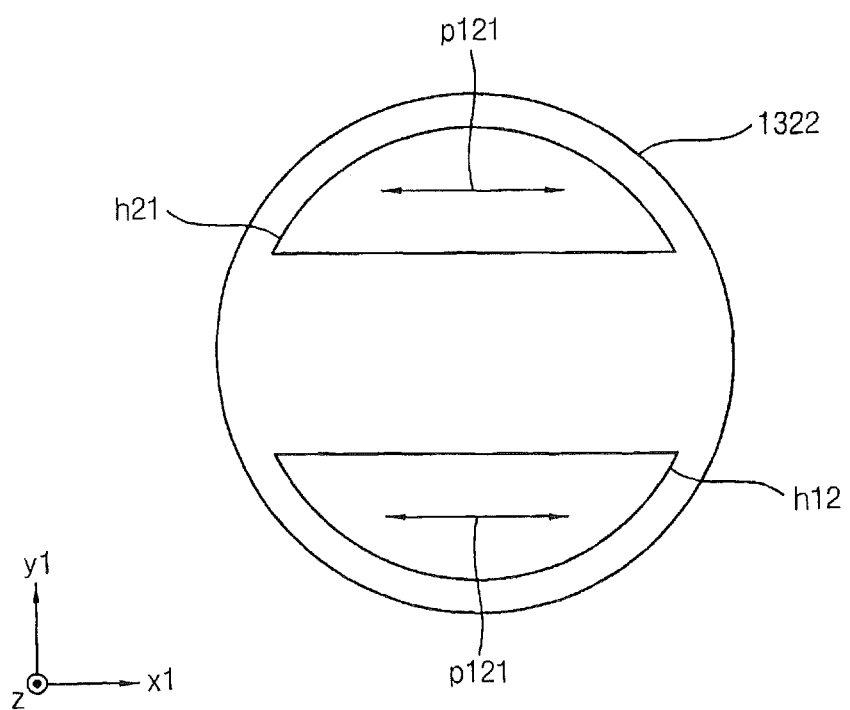

FIGS. 3A and 3B are cross-sectional views illustrating spatial filters of the apparatus in FIG. 1.

In FIG. 3A, a horizontal direction may be referred to as an x1 direction. A vertical direction may be referred to as a y1 direction. A direction substantially perpendicular to the x1 direction and the y1 direction may be referred to as a z direction. The z direction may correspond to an optical axis direction of the straight polarized beam p11 passing through the spatial filter 1321. A polarized direction of the straight polarized beam p11 may be referred to as a direction p111. The polarized direction p111 may be parallel to the y1 direction.

Referring to FIG. 3A, the spatial filter 1321 may have openings h11 at both edges of the spatial filter 1321 in the x1 direction substantially perpendicular to the polarized direction p111 of the straight polarized beam p11. Thus, a part of the straight polarized beam p11 may pass through the openings h11 of the spatial filter 1321. In contrast, the rest of the straight polarized beam p11 may be blocked by the spatial filter 1321.

In FIG. 3B, an x1 direction, a y1 direction and a z direction may correspond to the x1 direction, the y1 direction and the z direction in FIG. 3A, respectively. A polarized direction of the straight polarized beam p12 may be referred to as a direction p121. The polarized direction p121 may be parallel to the x1 direction.

Referring to FIG. 3B, the spatial filter 1322 may have openings h12 at both edges of the spatial filter 1322 in the y1 direction substantially perpendicular to the polarized direction p121 of the straight polarized beam p12. Thus, a part of the straight polarized beam p12 may pass through the openings h12 of the spatial filter 1322. In contrast, the rest of the straight polarized beam p12 may be blocked by the spatial filter 1322.

Referring to FIG. 2, the straight polarized beam p11 passing through the spatial filter 1321 may be guided to the PBS 134 through the total reflection mirror 1331. The straight polarized beam p12 passing through the spatial filter 1322 may be guided to the PBS 134 through the total reflection mirror 1332. The PBS 134 may convert the straight polarized beams p11 and p12 into coaxially straight polarized beams p11 and p12. The coaxially straight polarized beams p11 and p12 may be guided to the NBS 14. The NBS 14 may reflect the coaxially straight polarized beams p11 and p12 toward the condenser lens 15.

The relay lenses 121 and 122 may adjust a diameter of the light emitted from the light source 11 in order to match diameters of the coaxially straight polarized beams p11 and p12 with the condenser lens 15.

The condenser lens 15 may condense the coaxially straight polarized beams p11 and p12 on the object 500 on a stage 19.

FIGS. 4A and 4B are perspective views illustrating objects in FIG. 1.

In FIG. 4A, a depthwise direction may represent an x2 direction. A horizontal direction may represent a y2 direction. A vertical direction may represent a z direction. The x2 direction, the y2 direction and the z direction may correspond to the x1 direction, the y1 direction and the z direction in FIGS. 3A and 3B, respectively.

The object 500 may include a semiconductor substrate. A first pattern 501 extended in the x2 direction and a second pattern 502 extended in the y2 direction may be arranged on the object 500. The first pattern 501 may be referred to as a vertical pattern. The second pattern 502 may be referred to as a horizontal pattern.

The straight polarized beam p11 condensed by the condenser lens 15 may include two light fluxes in the x1 direction (x2 direction in FIG. 4A) by the openings h11 of the spatial filter 1321 in FIG. 3A. The condenser lens 15 may condense the two light fluxes in the straight polarized beam p11 in the x2 direction. A condensed direction of the two light fluxes in the straight polarized beam p11 may be substantially parallel to the first pattern 501 as the vertical pattern. This incident shape to the object 500 may be referred to as a parallel incident shape. A polarized direction of the straight polarized beam p11 may correspond to the y2 direction.

The straight polarized beam p12 condensed by the condenser lens 15 may include two light fluxes in the y1 direction (y2 direction in FIG. 4B) by the openings h12 of the spatial filter 1322 in FIG. 3B. The condenser lens 15 may condense the two light fluxes in the straight polarized beam p12 in the y2 direction. A condensed direction of the two light fluxes in the straight polarized beam p12 may be substantially perpendicular to the first pattern 501 as the vertical pattern. This incident shape to the object 500 may be referred to as a vertical incident shape. A polarized direction of the straight polarized beam p12 may correspond to the x2 direction.

The condensed straight polarized beams p11 and p12 may be reflected from the surface of the object 500. The surface of the object 500 may have different reflectivities in accordance with existences of the first pattern 501 or the second pattern 502. Signal intensities of the reflected lights may vary in accordance with condensed positions of the straight polarized beams p11 and p12 at which the first pattern 501 or the second pattern 502 may exist or not. Thus, whether the first pattern 501 or the second pattern 502 may exist at the condensed positions of the straight polarized beams p11 and p12 or not may be determined based on the signal intensities of the reflected lights.

In example embodiments, the object may not be restricted within the convex pattern in FIG. 4A. For example, as shown in FIG. 4B, a defect on a concave groove on the object 500 may be detected. A first concave groove 501a in the x2 direction and a second concave groove 502a may be formed on the object 500. The first concave groove 501a may correspond to the vertical pattern. The second concave groove 502a may correspond to the horizontal pattern.

When the straight polarized beams p11 and p12 are incident to the first and second concave grooves 501a and 502a, a component of the straight polarized beams p11 and p12 polarized in a widthwise direction of the concave grooves may readily reach at a bottom surface of the concave grooves. In contrast, a component of the straight polarized beams p11 and p12 polarized in a lengthwise direction of the concave grooves may not reach at the bottom surface of the concave grooves. The component of the straight polarized beams p11 and p12 polarized in the lengthwise direction of the concave grooves may be reflected from the bottom surface of the concave grooves.

For example, when the straight polarized beam p11 polarized in the y2 direction is incident to the first groove 501a arranged in the x2 direction, the straight polarized beam p11 may readily reach at the bottom surface of the first groove 501a. Thus, a defect on the first groove 501a may be readily detected using the straight polarized beam p11. In contrast, when the straight polarized beam p12 polarized in the x2 direction may be incident to the first groove 501a arranged in the x2 direction, the straight polarized beam p12 may not reach at the bottom surface of the first groove 501a. The straight polarized beam p12 may be reflected from the bottom surface of the first groove 501a. Therefore, a defect on the first groove 501a may not be easily detected using the straight polarized beam p12.

The object 500 may be positioned on a stage 19. The stage 19 may be moved in the x2 direction and the y2 direction. Thus, the object 500 may be horizontally moved in the x2 direction and the y2 direction with respect to condensed positions of the straight polarized beams p11 and p12. The surface of the object 500 may be scanned using the straight polarized beams p11 and p12.

The reflected lights reflected from the object 500 may be guided to the imaging lens 16 through the condenser lens 15 and the NBS 14. Hereinafter, the reflected light 21b may refer to light reflected from the object 500. The imaging lens 16 may project the reflected light 21b onto the light detector 180. Optical conjugation position may exist between the light detector 180 and the object 500. Thus, the measuring unit 10 may not be restricted within the above-mentioned structure.

The light detector 180 may detect the reflected lights imaged by the imaging lens 16. When a defect exists on the first groove 501a, the defect may be detected using the straight polarized beam p11 vibrated in the y2 direction. The rest of the reflected lights may function as to increase brightness of the image. Thus, a signal to noise (S/N) ratio may be decreased in proportion to a percentage of the rest of the lights so that contrast of the image may be reduced. This phenomenon may be substantially the same as that with respect to the vertical pattern. A defect on the second groove 502a may be detected using the straight polarized beam p12 vibrated in the x2 direction. The rest of the reflected lights may function to increase the brightness of the image.

In example embodiments, the reflected lights from the object 500 may include only the straight polarized beam p11 passing through the spatial filter 1321 and the straight polarized beam p12 passing through the spatial filter 1322. Other polarized lights among the light emitted from the light source 11 may be blocked by the spatial filters 1321 and 1322. Thus, the rest of the reflected lights may be decreased in amount. As a result, the S/N ratio may be improved using the filter unit 13.

When the light emitted from the light source 11 is not polarized, the light passing through the spatial filter 1321 may include polarized lights as well as the straight polarized beams p11 and p12. A signal-to-noise ratio using the straight polarized beam p11 may be referred to as an SHY. A signal-to-noise ratio using the rest of the polarized lights may be referred to as an SHH. A signal-to-noise using the straight polarized beam p12 may be referred to as an SVV. A signal-to-noise using the rest of the polarized lights may be referred to as an SVH.

When the light emitted from the light source 11 is not divided into the straight polarized beams p11 and p12, the signal-to-noise ratio may be an average of the SHY, the SHH, the SVV and the SVH. In contrast, when the light emitted from the light source 11 is divided into the straight polarized beams p11 and p12, the S/N ratio may be an average of the SHV and the SVH. When a defect on the first groove 501a in FIG. 4B may be detected, the SHV may be greater than the SHH, the SVV and the SVH. The average of the SHV and the SVH may be greater than the average of the SHV, the SHH, the SVV and the SVH. As a result, the S/N ratio using the straight polarized beams p11 and p12 may be improved compared when the light is not divided into the straight polarized beams p11 and p12.

The light detector 180 may create the image based on the signal intensities of the reflected lights from the object, which may be scanned by the straight polarized beams p11 and p12. The light detector 180 may output the image to the analyzing unit 20. In example embodiments, the light detector 180 may include a charge coupled device (CCD), a complementary metal oxide semiconductor (CMOS), a time delay integration (TDI) camera, etc. The TDI camera may rapidly scan the object 500 to obtain a clear image.

The analyzing unit 20 may receive the image obtained from the light detector 180. The analyzing unit 20 may compare the image with a reference image to obtain a difference between the image and the reference image. The reference image may correspond to an image of the object without a defect. Alternatively, a pattern without a defect may be formed. The pattern without the defect may be photographed to obtain the reference image. Further, images of adjacent cells or dies on the semiconductor substrate may be compared with each other to obtain a difference. The adjacent cells may be compared with each other to obtain the difference. Whether the defect may exist in any one of the adjacent cells may be determined based on the difference. This determination may be similarly applied to the comparison between the adjacent dies.

Figure 5:
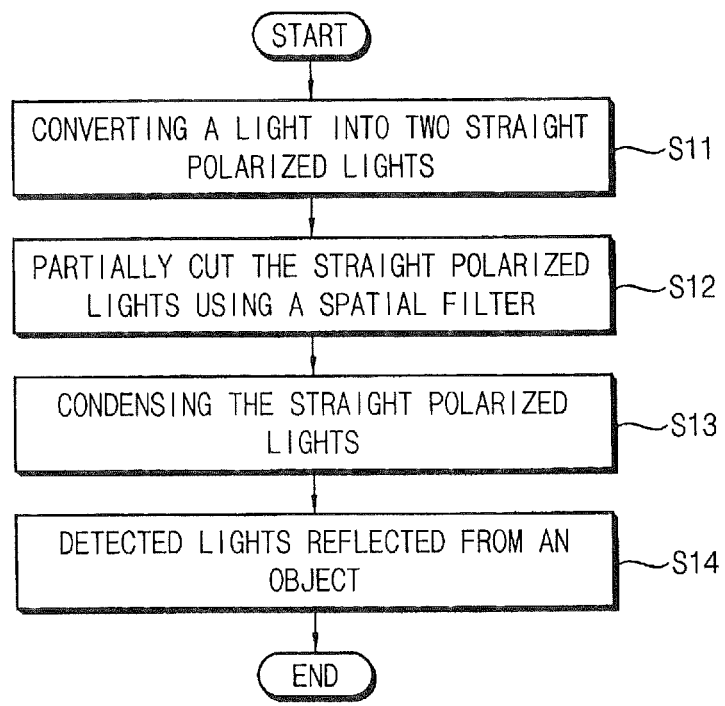

FIG. 5 is a flow chart illustrating a method of detecting a defect of an object using the apparatus in FIG. 1.

In step S11, the light emitted from the light source 11 may be converted into the straight light by the relay lenses 121 and 122. The straight light may be guided to the PBS 131. The PBS 131 may divide the straight light into the straight polarized beams p11 and p12 substantially perpendicular to each other. The straight polarized beam p11 may be incident to the spatial filter 1321. The straight polarized beam p12 may be incident to the spatial filter 1322.

In step S12, a part of the straight polarized beam p11 may pass through the opening h11 of the spatial filter 1321. The rest of the straight polarized beam p11 may be blocked by the spatial filter 1321.

A part of the straight light p12 may pass through the opening h12 of the spatial filter 1322. The rest of the straight polarized beam p12 may be blocked by the spatial filter 1322.

The straight polarized beam p11 passing through the spatial filter 1321 may be guided to the PBS 134 through the total reflection mirror 1331. The straight polarized beam p12 passing through the spatial filter 1322 may be guided to the PBS 134 through the total reflection mirror 1332. The PBS 134 may covert the straight polarized beams p11 and p12 into coaxially straight polarized beams p11 and p12. The coaxially straight polarized beams p11 and p12 may be guided to the NBS 14. The NBS 14 may reflect the coaxially straight polarized beams p11 and p12 toward the condenser lens 15.

In step S13, the condenser lens 15 may condense the coaxially straight polarized beams p11 and p12 on the object 500 arranged on the stage 19.

The condensed straight polarized beams p11 and p12 may be reflected from the surface of the object 500. The surface of the object 500 may have different reflectivities in accordance with the existence of the first pattern 501 or the second pattern 502 in FIG. 4A. Thus, the signal intensities of the reflected lights may vary in accordance with condensed positions of the straight polarized beams p11 and p12 at which the first pattern 501 or the second pattern 502 may exist or not.

When the straight polarized beams p11 and p12 are incident to the grooves 501a and 502a in FIG. 4B, the component of the straight polarized beams p11 and p12 polarized in the widthwise direction of the grooves 501a and 502a may easily reach at the bottoms of the grooves 501a and 502a. In contrast, the component of the straight polarized beams p11 and p12 polarized in the lengthwise direction of the grooves 501a and 502a may not reach at the bottoms of the grooves 501a and 502a. The component of the straight polarized beams p11 and p12 polarized in the lengthwise direction of the grooves 501a and 502a may be reflected from the bottoms of the grooves 501a and 502a.

Referring again to FIG. 2, in example embodiments, the object 500 may be positioned on the stage 19. The stage 19 may be moved in the x2 direction and the y2 direction. Thus, the object 500 may be horizontally moved in the x2 direction and the y2 direction with respect to condensed positions of the straight polarized beams p11 and p12. The surface of the object 500 may be scanned using the straight polarized beams p11 and p12.

In step S14, the lights reflected from the object 500 may be guided to the imaging lens 16 through the condenser lens 15 and the NBS 14. The imaging lens 16 may transmit the reflected light to the light detector 180.

The light detector 180 may detect the reflected light transmitted from the imaging lens 16. The light detector 180 may create the image based on the signal intensities of the reflected lights from the object, which may be scanned by the straight polarized beams p11 and p12. The light detector 180 may output the image to the analyzing unit 20.

According to this example embodiment, the defects on the vertical pattern and the horizontal pattern having the polarization dependence may be simultaneously detected. Further, because a percentage of the light not used for detecting the defect may be decreased by passing the light through the spatial filters, the S/N ratio with respect to the defect detection may be improved. Therefore, when the defect may exist in any one of the vertical pattern and the horizontal pattern, the defect may be accurately detected. Furthermore, because the defects in the vertical pattern and the horizontal pattern may be simultaneously detected, a time for detecting the defect may be remarkably reduced.

Figure 6:
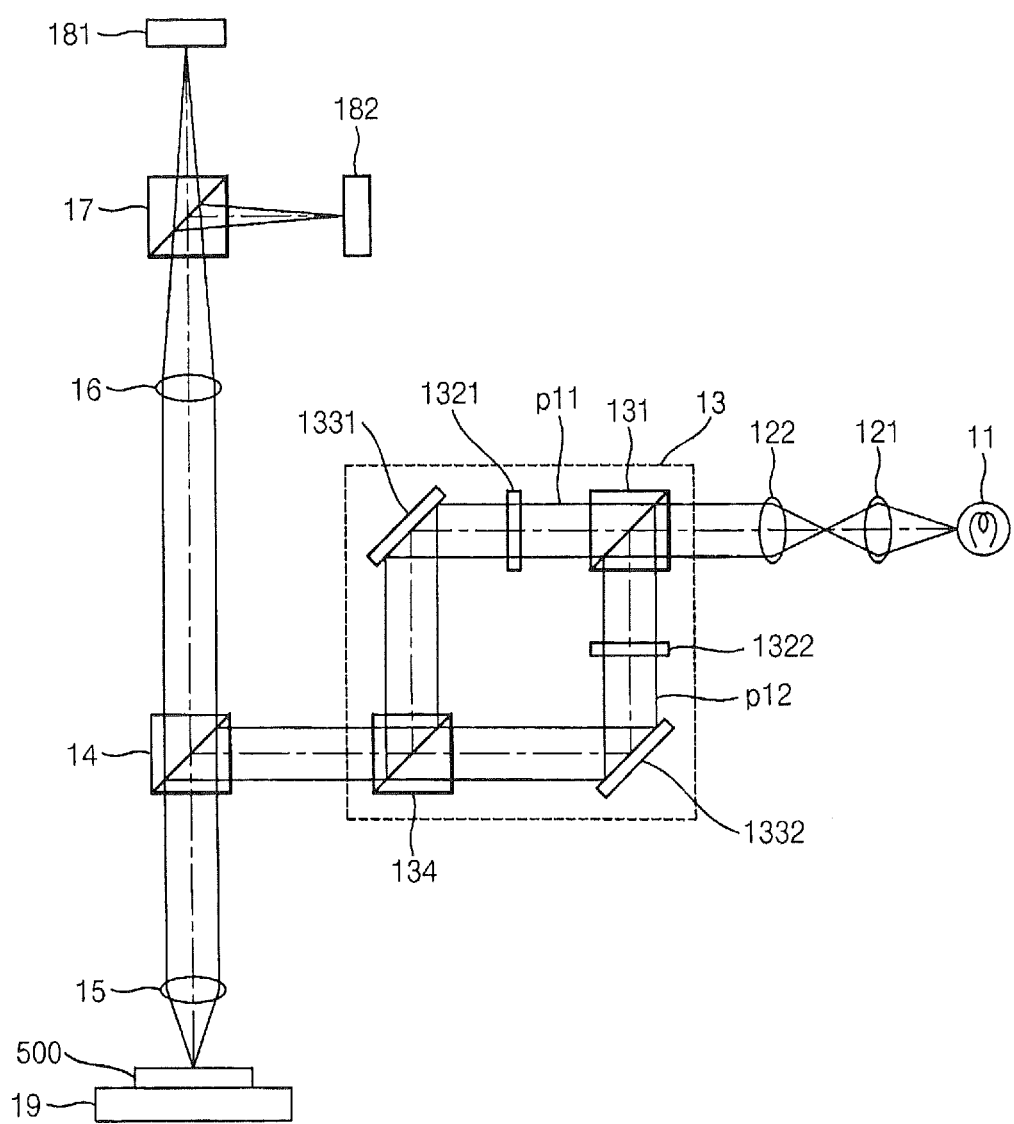

FIG. 6 is a schematic view illustrating a measuring unit in accordance with example embodiments.

A measuring unit 10a of this example embodiment may be substantially similar to measuring unit 10 in FIG. 2, except that the measuring unit 10a includes two light detectors 181 and 182. Thus, the same reference numerals may refer to the same elements and any further illustrations with respect to the same element may be omitted herein for brevity.

Referring to FIG. 6, the straight polarized beams p11 and p12 may be incident to the object 500. The reflected lights from the object may be guided to the PBS 17 through the condenser lens 15, the NBS 14 and the imaging lens 16. The PBS 17 may divide the reflected lights into two polarized lights substantially perpendicular to each other such as the straight polarized beams p11 and p12. Two light detectors 181 and 182 may separately detect the straight polarized beams p11 and p12. That is, the light detector 181 may detect the straight polarized beam p11. The light detector 182 may detect the straight polarized beam p12. The imaging lens 16 may provide the light detector 181 with the straight polarized beam p11 The imaging lens 16 may provide the light detector 182 with the straight polarized beam p12. The optical conjugation position may exist between the light detectors 181 and 182 and the object 500. Thus, the measuring unit 10a may not be restricted within the above-mentioned structure. Further, the structure of the PBS 17 may not be restricted within a specific structure. For example, lights passing through the NBS in place of the PBS 17 may pass through a polarizing filter to obtain the straight polarized beams p11 and p12.

The light detector 181 may create an image based on signal intensities of the reflected lights from the object, which may be scanned by the straight polarized beam p11. The light detector 182 may create an image based on signal intensities of the reflected lights from the object, which may be scanned by the straight polarized beam p12. The light detectors 181 and 182 may output the images to the analyzing unit 20.

The analyzing unit 20 may receive the image from the light detector 181 corresponding to the straight polarized beam p11. The analyzing unit 20 may receive the image from the light detector 182 corresponding to the straight polarized beam p12. The analyzing unit 20 may combine the two images with each other to detect a defect on the object 500.

In example embodiments, the analyzing unit 20 may compare the images with reference images, which may correspond to the straight polarized beams p11 and p12, respectively, to obtain differences between the images and the reference images. For example, a defect of the horizontal pattern, i.e., the first groove 501a in FIG. 4B, on the object 500 may be shown the comparison result obtained using the straight polarized beam p11 as the difference. In contrast, a defect of the vertical pattern, i.e., the second groove 502a in FIG. 4B, on the object 500 may be shown the comparison result obtained using the straight polarized beam p12 as the difference.

The analyzing unit 20 may detect the defect in case that the difference corresponding to the defect may exist in the comparison result obtained using the straight polarized beam p11 and the comparison result obtained using the straight polarized beam p12. Alternatively, the defect may be detected using other methods that may be capable of combining the image of the straight polarized beam p11 and the image of the straight polarized beam p12 with each other.

According to this example embodiment, the measuring unit 10a may divide the reflected lights into the straight polarized beams p11 and p12 substantially perpendicular to each other to obtain the images corresponding to the straight polarized beams p11 and p12. Thus, although any one of the straight polarized beams p11 and p12 may not be used for detecting the defect, it may not be required to increase brightness of the image used for detecting the defect. As a result, the S/N ratio with respect to the defect detection may be improved. Further, an accuracy of the defect detection may also be improved.

Figure 7A:
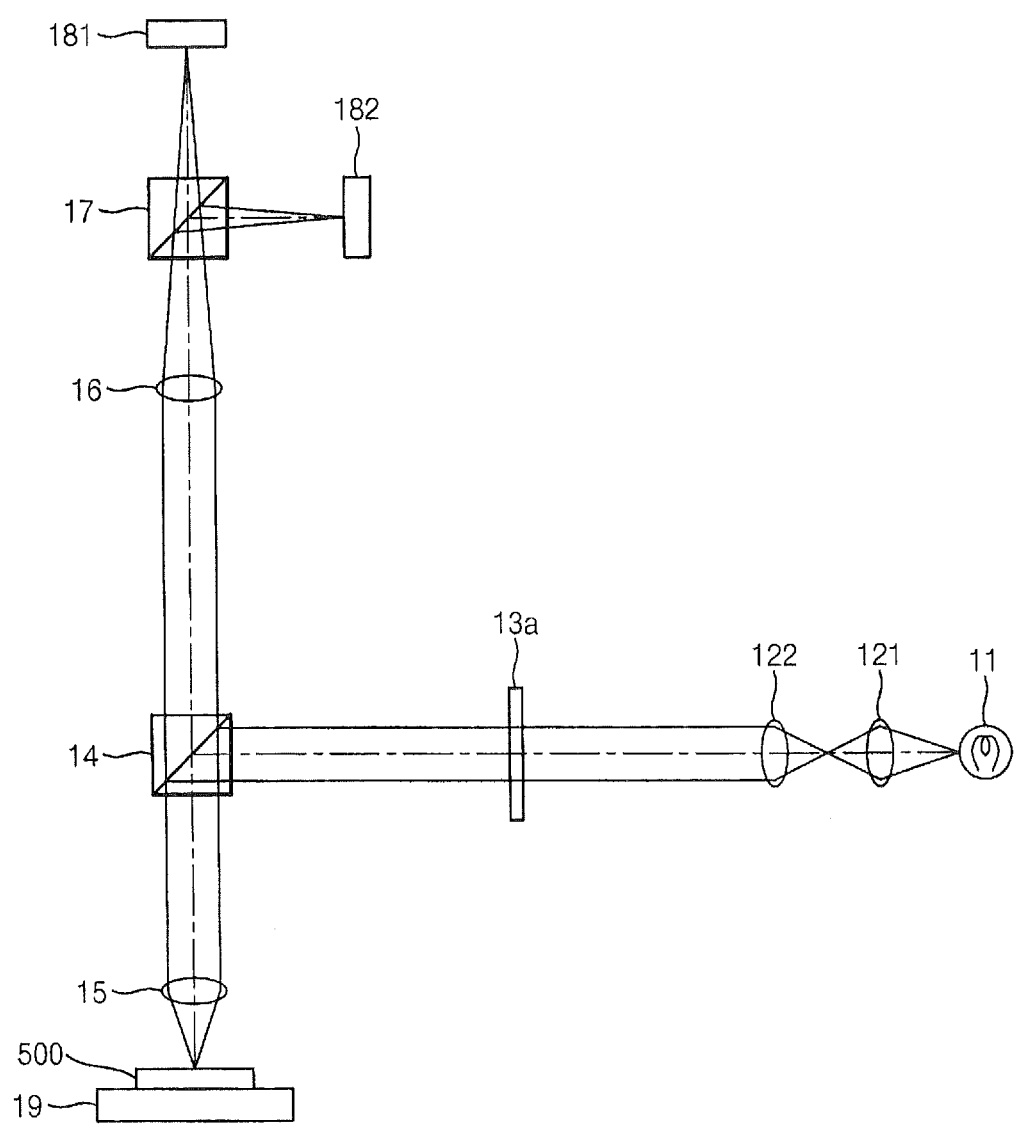
FIGS. 7A and 7B are cross-sectional views illustrating spatial filters in accordance with example embodiments.
Figure 7B:
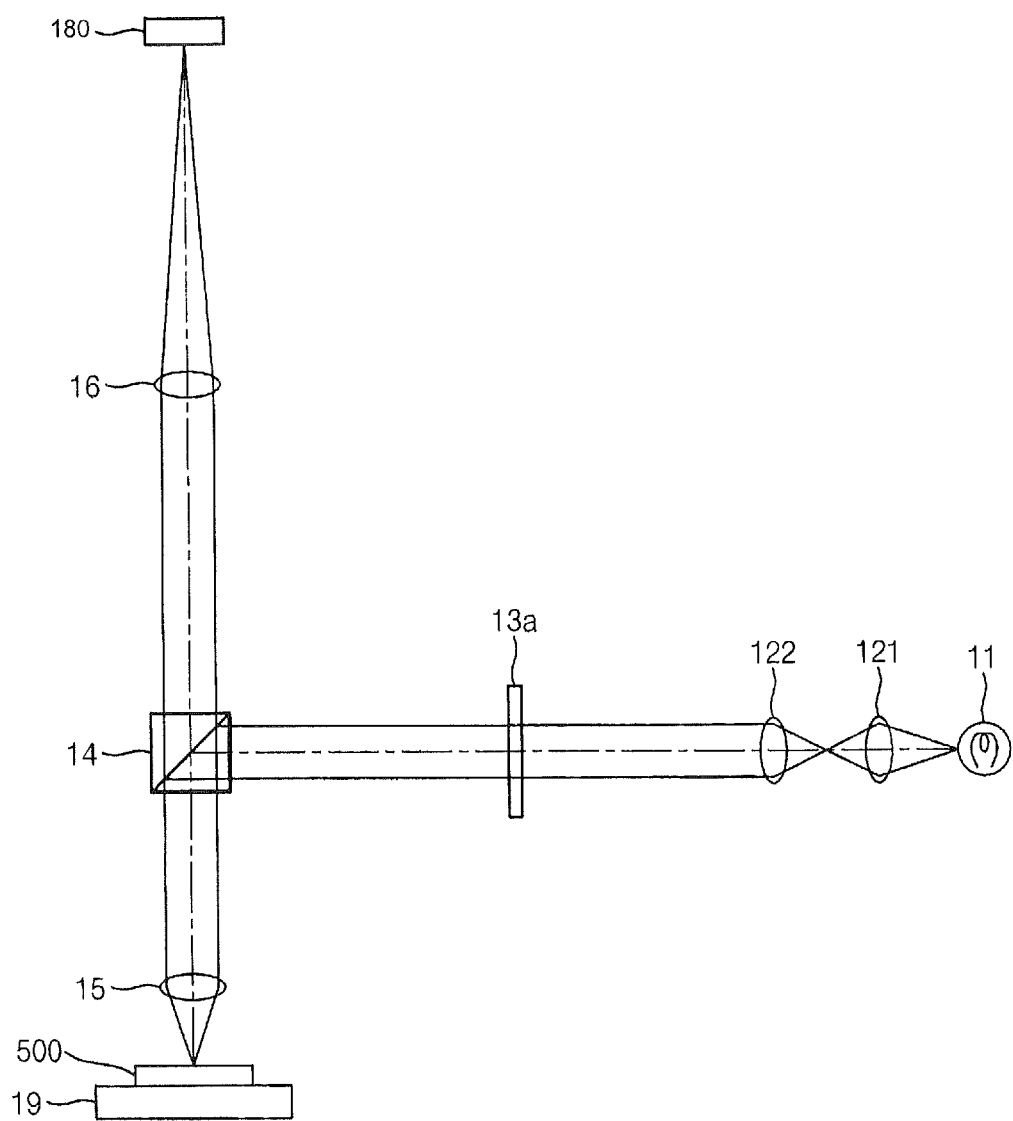
Figure 8A:
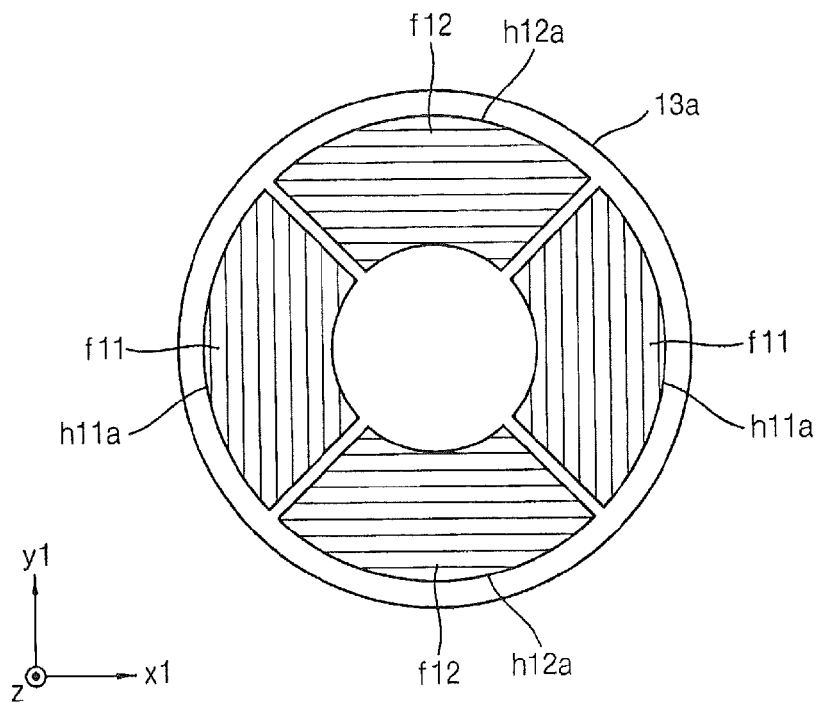
FIG. 8A is a cross-sectional view illustrating a composite filter in accordance with example embodiments.
Figure 8B:
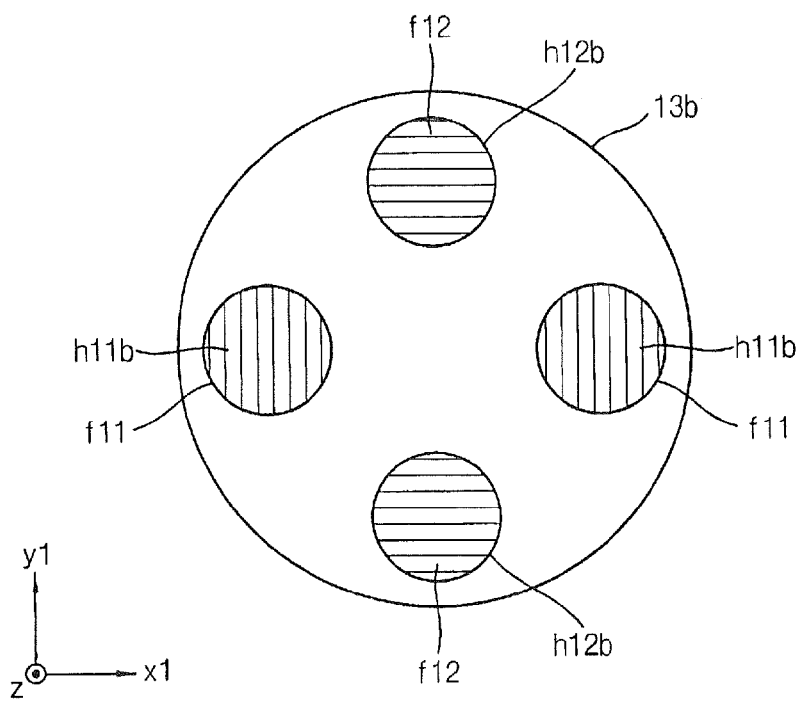
FIG. 8B is a cross-sectional view illustrating a composite filter in accordance with example embodiments.
Figure 8C:
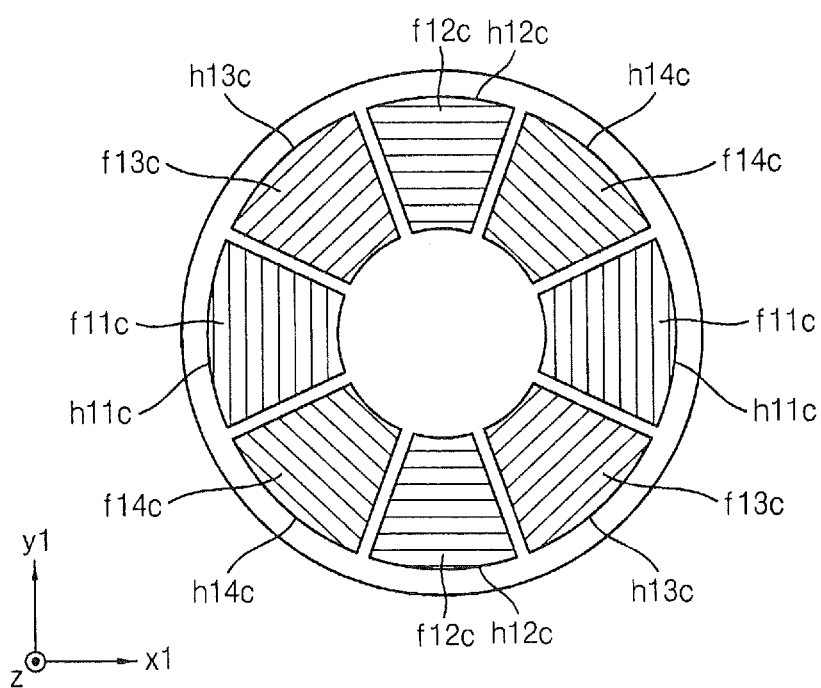
FIG. 8C is a cross-sectional view illustrating a composite filter in accordance with example embodiments.
Figure 9:
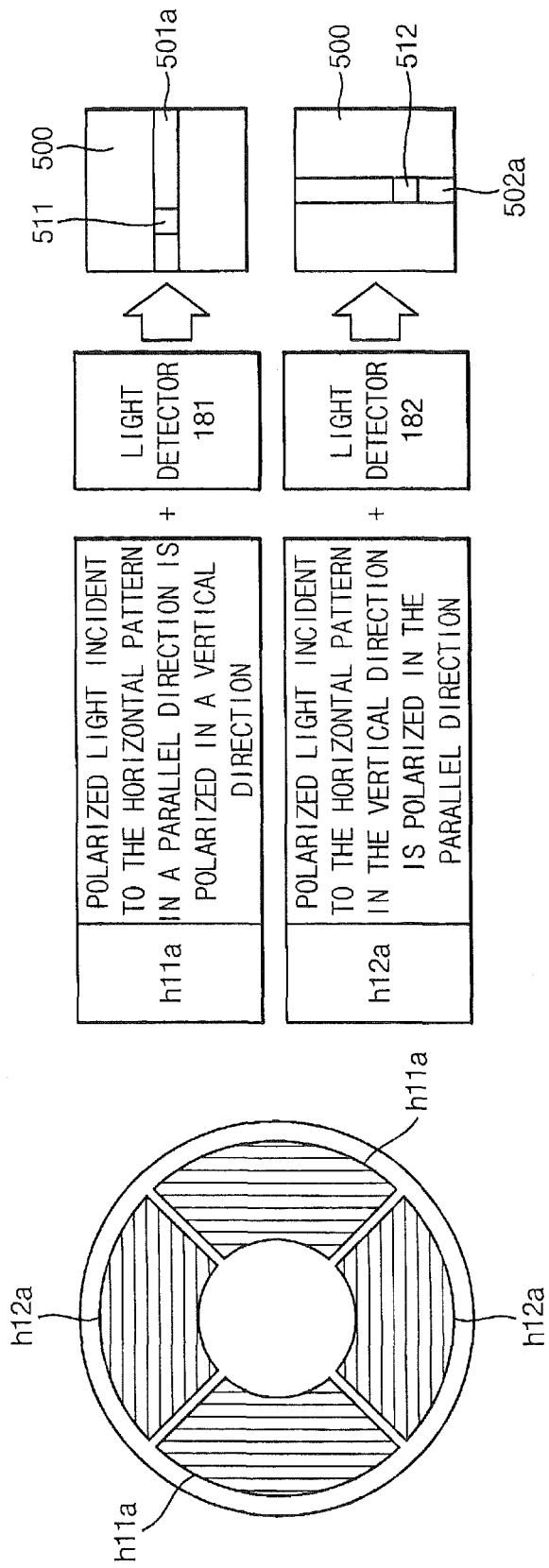

FIGS. 7A and 7B are cross-sectional views illustrating spatial filters in accordance with example embodiments, FIG. 8A is a cross-sectional view illustrating a composite filter in accordance with example embodiments, FIG. 8B is a cross-sectional view illustrating a composite filter in accordance with example embodiments, FIG. 8C is a cross-sectional view illustrating a composite filter in accordance with example embodiments, and FIG. 9 is a schematic view illustrating relations between an incident direction, a polarized direction and an object in accordance with example embodiments.

A measuring unit 10b of this example embodiment may be substantially similar to the measuring unit 10a in FIG. 6 except that the measuring unit 10b includes a filter unit. Thus, the same reference numerals may refer to the same elements and any further illustrations with respect to the same element may be omitted herein for brevity.

Referring to FIG. 7A, a filter unit of this example embodiment may include a composite filter 13a. The composite filter 13a may have characteristics of the spatial filters 1331 and 1332 and the PBS 131 and 134.

Referring to FIG. 8A, the composite filter 13a may have two openings h11a at edges of the composite filter 13a in the x1 direction. Polarizing portions f11 may be arranged in the openings h11, respectively. The polarizing portion f11 may polarize the light in the y1 direction. Thus, only a straight polarized beam p11a polarized in the y1 direction among the light emitted from the light source 11 may pass through the openings h11a. The straight polarized beam p11a may correspond to the straight polarized beam p11 in FIG. 6.

Further, the composite filter 13a may have two openings h12a at edges of the composite filter 13a in the y1 direction. Polarizing portions f12 may be arranged in the openings h12, respectively. The polarizing portion f12 may polarize the light in the x1 direction. Thus, only a straight polarized beam p12a polarized in the x1 direction among the light emitted from the light source 11 may pass through the openings h12a. The straight polarized beam p12a may correspond to the straight polarized beam p12 in FIG. 6.

In example embodiments, when the openings h11a and h12a and the polarizing portions f11 and f12 have the above-mentioned functions, the shapes of the openings h11a and h12a may not be restricted within the shape in FIG. 8A. Alternatively, as shown in FIG. 8B, the composite filter 13a may have circular openings h11b and h12b. The polarizing portions f11 and f12 may be arranged in the circular openings h11b and h12b.

Referring to FIG. 7A, the straight polarized beams p11a and p12a passing through the openings h11a of the composite filter 13a may be guided to the NBS 14. Following processes may be substantially similar to those illustrated with reference to FIG. 6.

Referring to FIG. 9, the straight polarized beam p11a passing through the opening h11a of the composite filter 13a may be parallely incident to the horizontal pattern. The straight polarized beam p11a may be objected from the object 500. The light detector 181 may detect the reflected light from the object 500. When the straight polarized beam p11a is incident to the horizontal pattern, the straight polarized beam p11a may be polarized with respect to the horizontal pattern in the vertical direction. As shown in FIG. 4B, the horizontal pattern may include the first groove 501a. Because the straight polarized beam p11a may be polarized in the widthwise direction of the first groove 501a, the straight polarized beam p11a may readily reach at the bottom surface of the first groove 501a. Thus, a defect 511 on the horizontal pattern may be easily detected using the straight polarized beam p11a passing through the opening h11a.

The straight polarized beam p12a passing through the opening h12a of the composite filter 13a may be vertically incident to the vertical pattern. The straight polarized beam p12a may be objected from the object 500. The light detector 182 may detect the reflected light from the object 500. When the straight polarized beam p12a is incident to the vertical pattern, the straight polarized beam p12a may be polarized with respect to the vertical pattern in the vertical direction. As shown in FIG. 4B, the vertical pattern may include the second groove 502a. Because the straight polarized beam p12a may be polarized in the widthwise direction of the second groove 502a, the straight polarized beam p12a may readily reach at the bottom surface of the second groove 502a. Thus, a defect 512 on the vertical pattern may be easily detected using the straight polarized beam p12a passing through the opening h12a.

Referring to FIG. 7B, a measuring unit 10c including the composite filter 13a may include the single light detector 180. That is, the measuring unit 10c may include the single light detector 180 in place of the PBS 17 and the light detectors 181 and 182 in FIG. 7A. The analyzing unit 20a may be operated substantially the same as those of the analyzing unit 20a in FIG. 2.

When the single light detector 180 may detect the defect, polarized directions of the light emitted from the light source 11 may not be restricted within the x1 direction and the y1 direction. For example, a composite filter 13c in FIG. 8C may be used in place of the composite filter 13a or 13b. The composite filter 13c may have openings h11c to h14c arranged in a circumferential direction. The openings h11c to h14c may be symmetrical with each other with respect to a center point of the composite filter 13c.

Polarizing portions f11c to f14c may be arranged in the openings h11c to hl1c, respectively. The polarizing portions f11c to f14c may be extended in a direction substantially perpendicular to the opposite direction of pair of the symmetrically arranged openings h11c to h14c. The light passing through the openings h11c to h14c may be divided into straight polarized beams p11c to pl4c.

Any one of the straight polarized beams p11c to p14c, which may have a polarized direction substantially perpendicular to the lengthwise direction of the pattern on the object 500, may be used for detecting the defect. Thus, defects in every direction may be detected without direction restrictions of the defects. Further, the polarizing portions f11c to f14c may block polarized components of the light except for the straight polarized beams p11c to p14c. Therefore, an amount of the light not used for detecting the defect may be decreased so that the S/N ratio with respect to the defect detection may be improved. In FIG. 8C, the composite filter 13c may have the eight openings h11c to h14c to obtain the four kinds of the straight polarized beams p11c to p14c. However, the numbers of the openings may not be restricted within a specific number. The numbers of the openings and the kinds of the straight polarized lights may be determined in accordance with directions and numbers of the patterns of the object.

According to this example embodiment, the measuring unit 10c may include the composite filter 13a. Thus, the measuring unit 10b may have a small size with the above-mentioned functions substantially similar to those of the measuring unit 10a in FIG. 6.

Figure 10:
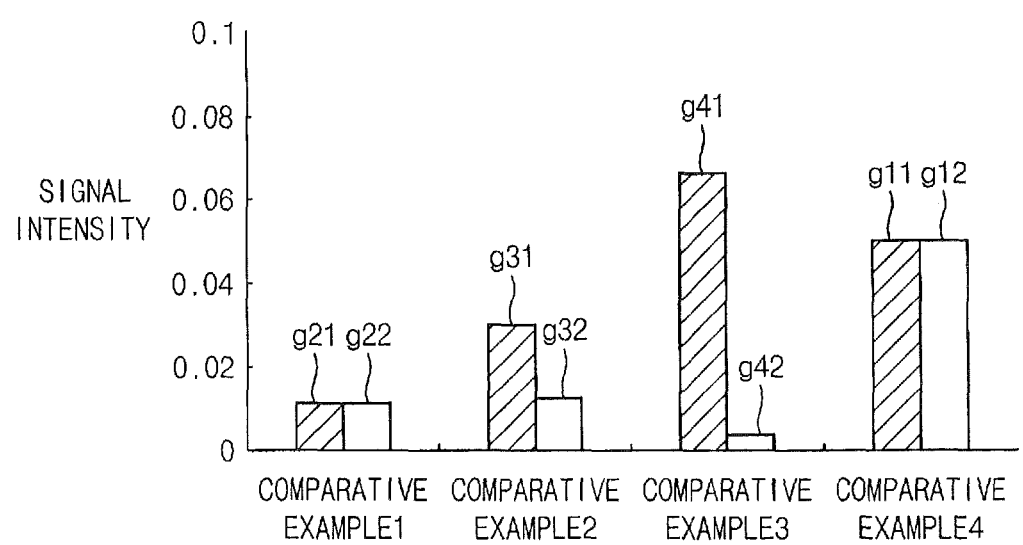

FIG. 10 is a graph showing signal intensities by comparative examples.

In FIG. 10, a vertical axis may represent signal intensities by defect detections. Graphs g11 and g12 in Comparative Example 4 may represent signal intensities using the apparatus of example embodiments. The graph g11 may represent the signal intensity when a defect on the horizontal pattern may be detected. The graph g12 may represent the signal intensity when a defect on the vertical pattern may be detected.

Comparative Example 1 may use a bright field image method. In Comparative Example 1, a non-polarized light emitted from a light source may be reflected from an object. A single light detect may detect the reflected light to obtain an image. A defect may be detected based on the image. A graph g21 may represent a signal intensity when a defect on the horizontal pattern may be detected. A graph g22 may represent a signal intensity when a defect on the vertical pattern may be detected.

Comparative Example 2 may use the spatial filter 1321 in FIG. 3A. In Comparative Example 2, a non-polarized light emitted from a light source may pass through the opening h11 of the spatial filter 1321. A graph g31 may represent a signal intensity when a defect on the horizontal pattern may be detected. A graph g32 may represent a signal intensity when a defect on the vertical pattern may be detected.

Comparative Example 3 may use the spatial filter 1321 in FIG. 3A. In Comparative Example 3, a straight polarized light polarized in the y1 direction may pass through the opening h11 of the spatial filter 1321. A graph g41 may represent a signal intensity when a defect on the horizontal pattern may be detected. A graph g42 may represent a signal intensity when a defect on the vertical pattern may be detected.

As shown in FIG. 10, it may be noted that Comparative Example 1 may shown the lowermost signal intensity. As mentioned above, the rest of the light not used for detecting the defect may function as to increase the brightness. That is, the rest of the light not used for detecting the defect may increase the S/N ratio. Thus, it may be noted that an amount of the rest of the light in Comparative Example 1 may have the highest percentage compared to Comparative Examples 2 to 4.

Comparative Example 2 may have the signal intensity with respect to the defect on the horizontal pattern higher than that in Comparative Example 1. Thus, it may be noted that the rest of the light not used for detecting the defect may be blocked by the spatial filter 1321.

Comparative Example 3 may have the signal intensity with respect to the defect on the horizontal pattern higher than that in Comparative Example 2 and the signal intensity with respect to the defect on the vertical pattern lower than that in Comparative Example 2. Thus, it may be noted that the straight polarized light polarized in the vertical direction with respect to the horizontal pattern may contribute to the detection of the defect on the horizontal pattern, not contribute to the detection of the defect on the vertical pattern.

The signal intensity in Comparative Example 4 with respect to the defect on the horizontal pattern may be higher than those in Comparative Example 1 and 2, although slightly lower than that in Comparative Example 3. Further, the signal intensity in Comparative Example 4 with respect to the defect on the horizontal pattern may be substantially the same as that with respect to the defect on the vertical pattern. Thus, it may be noted that the signal intensity in Comparative Example 4 with respect to the defect on the vertical pattern may be higher than those in Comparative Examples 1 to 3. Thus, when the defect may be detected using an apparatus in Comparative Example 3, only the defect on the horizontal pattern may be detected. As a result, after changing the direction of the object, it may be required to perform the defect detection using the apparatus in Comparative Example 3. In contrast, the defects on the horizontal pattern and the vertical pattern may be simultaneously detected using the apparatus in Comparative Example 4. As a result, a time for detecting the defects on the horizontal pattern and the vertical pattern using the apparatus in Comparative Example 4 may be halved compared to a time for detecting the defects on the horizontal pattern and the vertical pattern using the apparatus in Comparative Example 3. Further, the signal intensities in Comparative Example 4 may be higher than those in Comparative Examples 1 and 2.

The composite filter 13a in the measuring unit 10b may be equivalent to the composite filter 13 in the measuring unit 10a. Thus, the results obtained using the measuring unit 10b may be substantially similar to those obtained using the measuring unit 10a.

Figure 11:
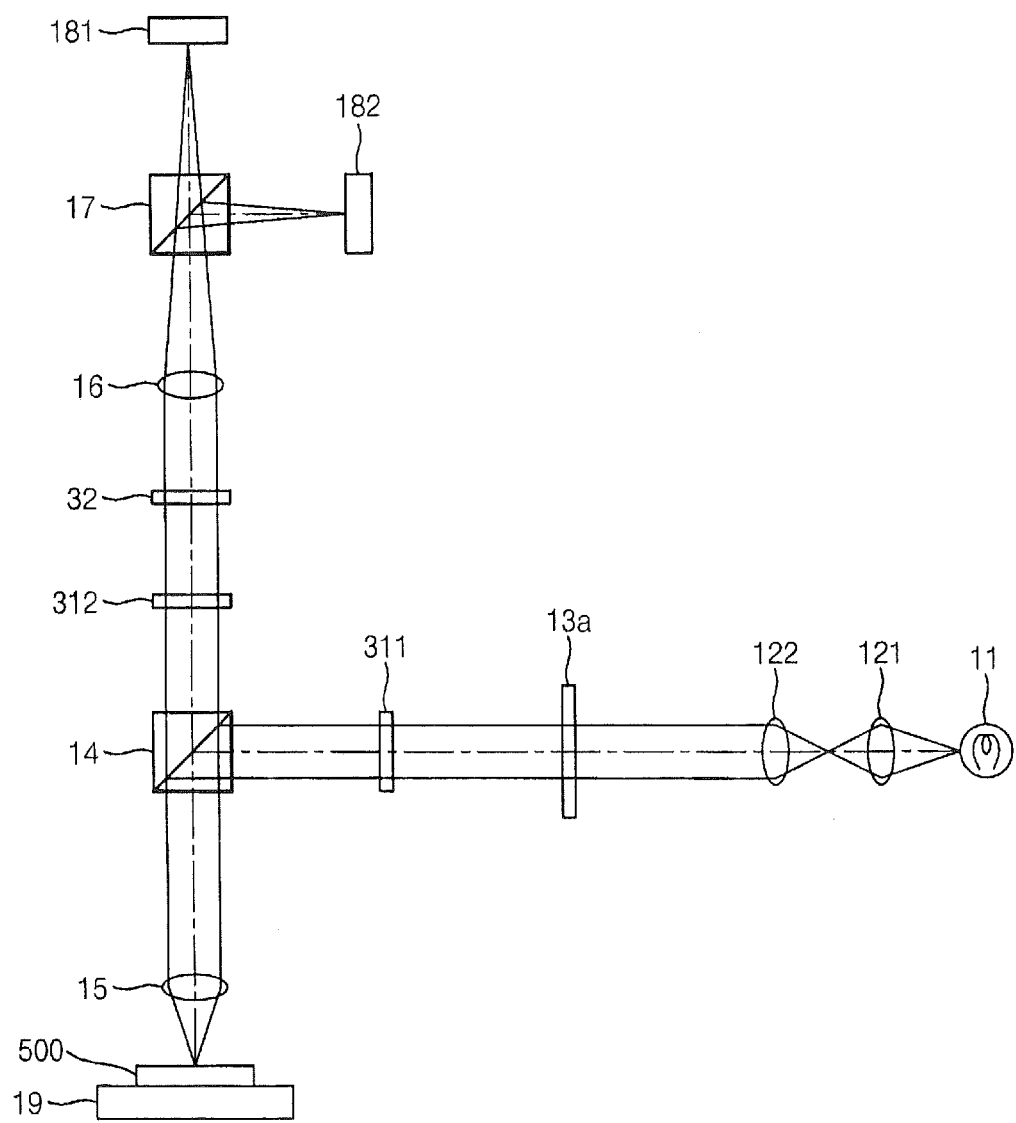

FIG. 11 is a schematic view illustrating a measuring unit in accordance with example embodiments.

A measuring unit 10c of this example embodiment may include substantially the same as those of the measuring unit 10b in FIG. 7A except for further including ½ wavelength plates and a total reflection cut filter. Thus, the same reference numerals may refer to the same elements and any further illustrations with respect to the same element may be omitted herein for brevity.

Referring to FIG. 11, the ½ wavelength plate 311 may be detachably arranged between the composite filter 13a and the NBS 14. The ½ wavelength plate 311 may provide phases of the straight polarized beams p11a and p12a passing through the composite filter 13a with a ½ wavelength. Thus, the straight polarized beams p11a and p12a may be changed to a desired angle with respect to the object 500.

The ½ wavelength plate 312 may be detachably arranged between the NBS 14 and the imaging lens 16. The ½ wavelength plate 312 may provide the reflected lights from the object 500 with a ½ wavelength. Thus, imaging directions of the straight polarized beams p11a and p12a to the light detectors 181 and 182 may be changed to a desired angle The regular reflection cut filter 32 may be detachably arranged between the ½ wavelength plate 312 and the imaging lens 16. The regular reflection cut filter 32 may cut a regularly reflected light in the straight polarized beams p11a and p12a.

Figure 12:
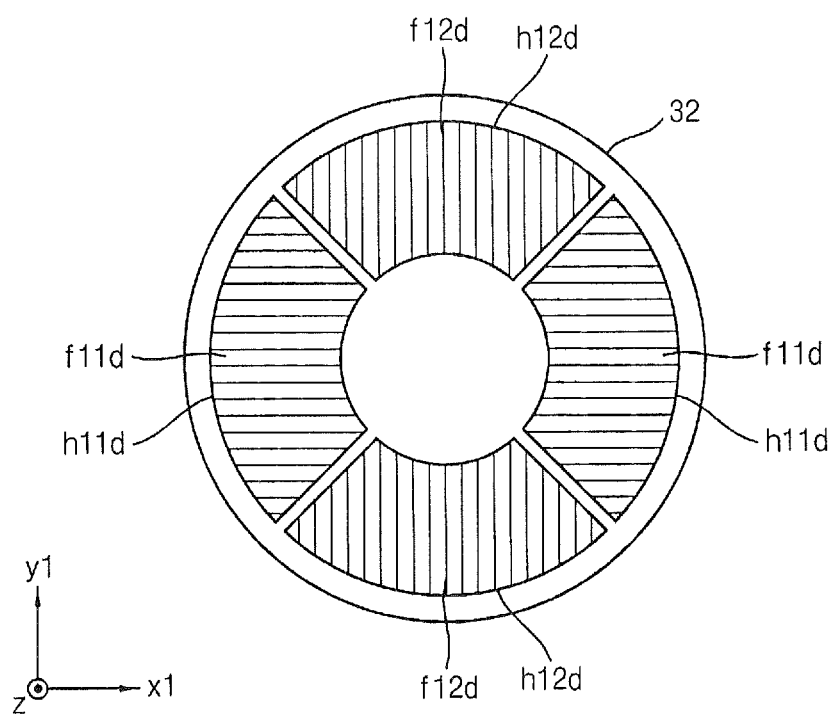

FIG. 12 is a cross-sectional view illustrating a regular reflection cut filter in accordance with example embodiments.

In FIG. 12, an x1 direction may represent a horizontal direction. A y1 direction may represent a vertical direction. A z direction may be substantially perpendicular to the x1 direction and the y1 direction. The z direction may correspond to an optical axis direction of the reflected lights from the object 500. The x1 direction and the y1 direction may correspond to the x1 direction and the y1 direction in FIG. 8A, respectively.

Referring to FIG. 12, the regular reflection cut filter 32 may have two openings h11d at edge of the regular reflection cut filter 32 in the x1 direction. A polarizing portion f11d may be arranged in the openings h11d along the x1 direction. Only the straight polarized light polarized in the x1 direction may pass through the openings h11d.

The regular reflection cut filter 32 may have two openings h12d at edge of the regular reflection cut filter 32 in the y1 direction. A polarizing portion f12d may be arranged in the openings h12d along the y1 direction. Only the straight polarized light polarized in the y1 direction may pass through the openings h12d.

After the straight polarized beam p11a may pass through the openings h11a in FIG. 8A, the straight polarized beam p11a may be incident to the object 500. The reflected light from the object 500 may be incident to the openings h11d of the regular reflection cut filter 32. Thus, a regularly reflected light may not pass through the openings h11d. Further, after the straight polarized beam p12a may pass through the openings h12a in FIG. 8A, the straight polarized beam p12a may be incident to the object 500. The reflected light from the object 500 may be incident to the openings h12d of the regular reflection cut filter 32. Thus, a regularly reflected light may not pass through the openings h12d.

In example embodiments, the regular reflection cut filter 32 may be located at a rear portion of the condenser lens 15. Thus, the position of the regular reflection cut filter 32 may not be restricted within a specific position. For example, as shown in FIG. 11, the regular reflection cut filter 32 may be located before the PBS 17. Alternatively, the regular reflection cut filter 32 may be located after the PBS 17. Further, when the regularly reflected light of the straight polarized lights may be blocked, a structure of the regular reflection cut filter 32 may not restricted.

As mentioned above, the regularly reflected light of the straight polarized beams p11a and p12a may be blocked using the regular reflection cut filter 32 to obtain a dark field image.

In example embodiments, the measuring unit 10c may include any one of the ½ wavelength plates 311 and 312 and the regular reflection cut filter 32.

In example embodiments, the measuring unit 10c may include the composite filter 13a. Alternatively, the measuring unit 10c may include the filter units in FIGS. 2 and 6 or the composite filter 13b in FIG. 8B.

In example embodiments, the measuring unit 10c may include the PBS 17 and the light detectors 181 and 182. Alternatively, the measuring unit 10c may include the single light detector 180 in FIG. 2 or 7B. The analyzing unit 20a may be operated substantially the same as the analyzing unit 20. Further, when the reflected light may be detected using the single light detector 180, the composite filter 13c in FIG. 8C in place of the composite filter 13a may be applied.

Figure 13:
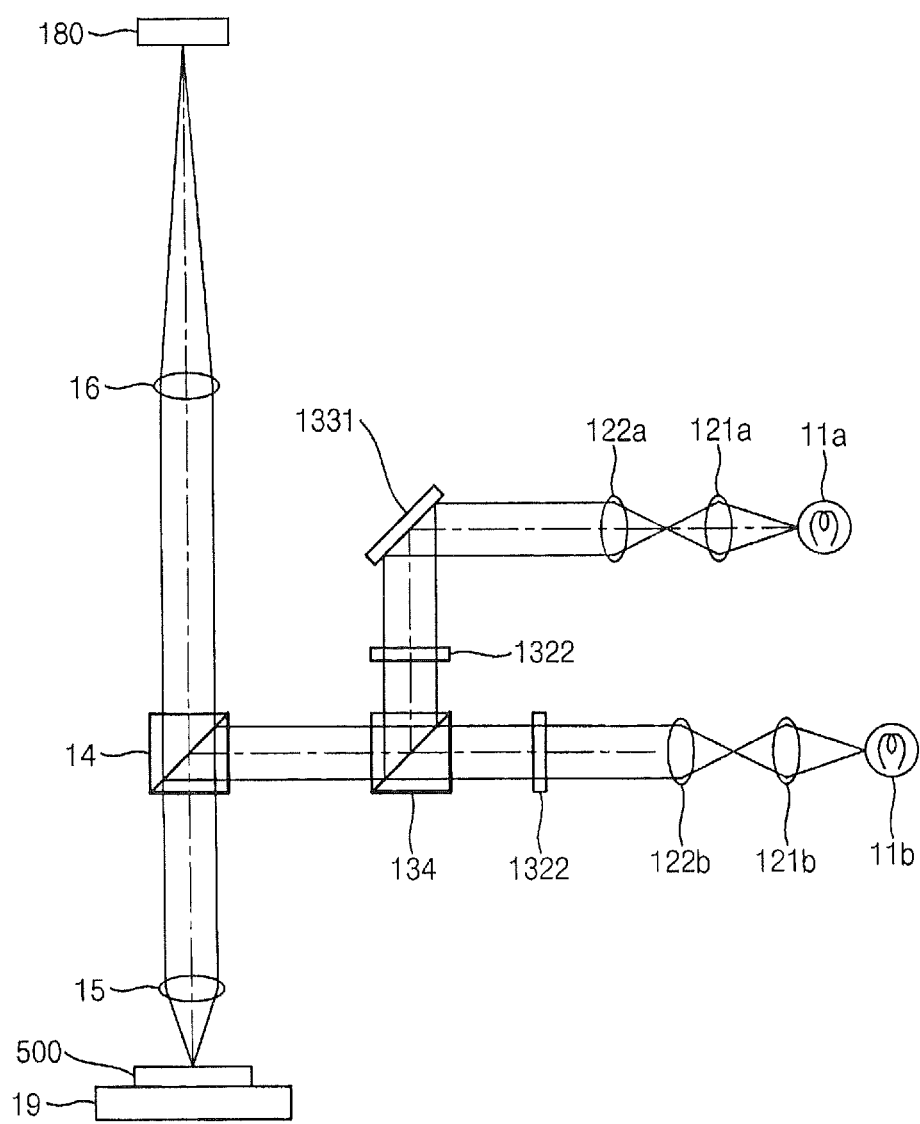

FIG. 13 is a cross-sectional view illustrating a measuring unit in accordance with example embodiments.

Referring to FIG. 13, a measuring unit 103 of this example embodiment may include two light sources 11a and 11b. The light sources 11a and 11 b may emit two straight polarized lights having different polarizing directions. Thus, the same reference numerals may refer to the same elements and any further illustrations with respect to the same elements may be omitted herein for brevity.

As mentioned above, the light sources 11a and 11b may emit the straight polarized lights having the different polarizing directions. The light sources 11a and 11b may include a laser source configured to emit a straight polarized light. Alternatively, the light sources 11a and 11b may include a light source configured to emit a non-polarized light, and a polarizing filter configured to polarize the non-polarized light. The straight polarized light emitted from the light source 11a may correspond to the straight polarized beam p11 divided by the PBS 131 in FIG. 2. The straight polarized light emitted from the light source 11b may correspond to the straight polarized beam p12 divided by the PBS 131 in FIG. 2.

The straight polarized beam p11 emitted from the light source 11a may be converted into parallel lights by the relay lenses 121a and 122a. The parallel lights may be guided to the spatial filter 1321 through the total reflection mirror 1331. The spatial filter 1321 may be substantially the same as the spatial filter 1321 in FIG. 3A. A part of the straight polarized beam p11 incident to the spatial filter 1321 may pass through the openings h11. In contrast, the rest of the straight polarized beam p11 may be blocked by the spatial filter 1321. The straight polarized beam p11 passing through the spatial filter 1321 may be guided to the PBS 134. The PBS 134 may be substantially the same as the PBS 134 in FIG. 2.

The straight polarized beam p12 emitted from the light source 11b may be converted into parallel lights by the relay lenses 121b and 122b. The parallel lights may be guided to the spatial filter 1322 through the total reflection mirror 1332. The spatial filter 1322 may be substantially the same as the spatial filter 1322 in FIG. 3B. A part of the straight polarized beam p12 incident to the spatial filter 1322 may pass through the openings h12. In contrast, the rest of the straight polarized beam p12 may be blocked by the spatial filter 1322. The straight polarized beam p12 passing through the spatial filter 1322 may be guided to the PBS 134. The straight polarized beams p11 and p12 may be guided to the NBS 14. Following processes after the NBS 14 may be substantially the same as those illustrated in above-mentioned example embodiments.

In example embodiments, the measuring unit 10e may include the single light detector 180. Alternatively, the measuring unit 10e may include the PBS 17 and the light detectors 181 and 182.

Further, the measuring unit 10e may further include any one of ½ wavelength plates 311 and 312 and the regular reflection cut filter 32.

According to this example embodiment, the measuring unit 10e may include the light sources 11a and 11b configured to separately emit the straight polarized lights having the different polarizing directions to obtain the straight polarized beams p11 and p12. The measuring unit 10e may use the straight polarized lights substantially the same those used in the measuring unit 10 by passing the straight polarized beams p11 and p12 through the spatial filters 1321 and 1322 and the PBS 134. Thus, the measuring unit 10e may have functions substantially the same as those of the measuring unit 10.

Figure 14:
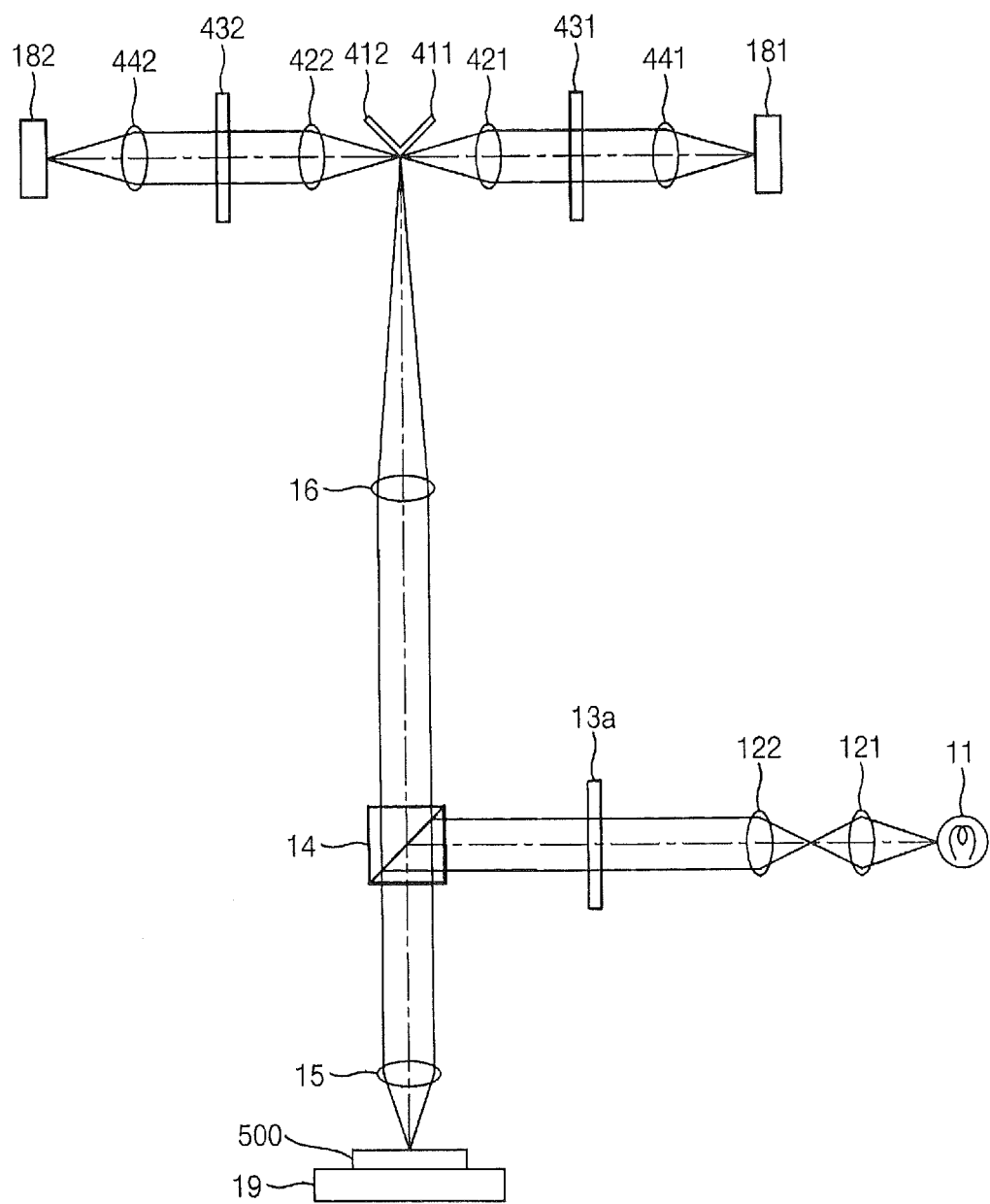

FIG. 14 is a cross-sectional view illustrating a measuring unit in accordance with example embodiments.

Referring to FIG. 14, a measuring unit 10f of this example embodiment may include a reflecting mirror 41 in place of the PBS 17 in FIG. 7A. The reflecting mirror 41 may include a total reflection mirror.

The straight polarized beams p11 and p12 may be incident to the object 500. The reflected lights from the object 500 may be guided to the reflecting mirror 41 through the condenser lens 15, the NBS 14 and the imaging lens 16.

In example embodiments, the reflecting mirror 41 may have opposite reflecting faces 411 and 412. The reflecting faces 411 and 412 of the reflecting mirror 41 may divide the reflected lights into light fluxes. A part of the reflected lights may be reflected from the reflecting face 411. The rest of the reflected lights may be reflected from the reflecting face 412.

The part of the reflected lights may be guided to a polarizing filter 431 through a relay lens 421. The polarizing filter 431 may include a polarizing portion configured to polarize a part of the reflected lights in the y1 direction. Thus, only the straight polarized beam p11a polarized in the y1 direction may pass through the polarizing filter 431. The imaging lens 441 may transmit the straight polarized beam p11a to the light detector 181. Thus, the light detector 181 may detect only the straight polarized beam p11a in the reflected lights reflected from the reflecting face 411.

The rest of the reflected lights may be guided to a polarizing filter 432 through a relay lens 422. The polarizing filter 432 may include a polarizing portion configured to polarize a part of the reflected lights in the x1 direction. Thus, only the straight polarized beam p12a polarized in the x1 direction may pass through the polarizing filter 432. The imaging lens 442 may transmit the straight polarized beam p12a to the light detector 182. Thus, the light detector 182 may detect only the straight polarized beam p12a in the reflected lights reflected from the reflecting face 412. Following processes may be substantially the same those in the measuring unit 10b.

In example embodiments, the reflected lights may be divided into the light fluxes. The divided light fluxes may be individually polarized. The light detectors 181 and 182 may detect the polarized lights. Thus, the light detectors 181 and 182 may detect other regions of the object 500 at a time. However, the whole regions of the object 500 may be detected using the light detectors 181 and 182 by scanning the object 500 with the reflected lights.

In example embodiments, the measuring unit 10f may include the composite filter 13a. Alternatively, the measuring unit 10f may include the filter unit 13 in FIGS. 2 and 6 or the composite filter 13b in FIG. 8B.

Further, the measuring unit 10f may further include any one of ½ wavelength plates 311 and 312 and the regular reflection cut filter 32.

According to this example embodiment, the reflected lights may be divided into the light fluxes using the reflecting mirror 41. The light fluxes may pass through the polarizing filters 431 and 432 to obtain the straight polarized beams p11a and p12a. Because the light detectors 181 and 182 may detect the straight polarized beams p11a and p12a, the S/N ratio may be improved and the accuracy of the defect detection may also improved.

The measuring unit 10e may include the light sources 11a and 11b configured to separately emit the straight polarized lights having the different polarizing directions to obtain the straight polarized beams p11 and p12. The measuring unit 10e may use the straight polarized lights substantially the same those used in the measuring unit 10 by passing the straight polarized beams p11 and p12 through the spatial filters 1321 and 1322 and the PBS 134. Thus, the measuring unit 10e may have functions substantially the same as those of the measuring unit 10.

The foregoing is illustrative of example embodiments and is not to be construed as limiting thereof. Although a few example embodiments have been described, those skilled in the art will readily appreciate that many modifications are possible in the example embodiments without materially departing from the novel teachings and advantages of the present invention. Accordingly, all such modifications are intended to be included within the scope of the present invention as defined in the claims. In the claims, means-plus-function clauses are intended to cover the structures described herein as performing the recited function and not only structural equivalents but also equivalent structures. Therefore, it is to be understood that the foregoing is illustrative of various example embodiments and is not to be construed as limited to the specific example embodiments disclosed, and that modifications to the disclosed example embodiments, as well as other example embodiments, are intended to be included within the scope of the appended claims.

What is claimed is:

1. An apparatus for detecting a defect of an object, the apparatus comprising:
   a light emitter configured to emit polarized beams of light having different polarized directions;
   a spatial filter having openings through which the polarized beams of light selectively pass;
   an optical member configured to condense the polarized beams of light and to project the beams of light onto the object; and
   a light detector configured to detect light reflected from the object;
   wherein the spatial filter has a first opening and a second opening therein, wherein a first polarizing portion configured to polarize straight polarized lights in a first direction is arranged in the first opening, and a second polarizing portion configured to polarize the straight polarized lights in a second direction different from the first direction is arranged in the second opening.

2. The apparatus of claim 1, wherein the light emitter comprises:
   a light source configured to emit a non-polarized light; and
   a polarizing filter configured to convert the non-polarized light into the polarized beams of light.

3. The apparatus of claim 2, wherein the polarizing filter is configured to provide the polarized beams of light with perpendicular polarizing directions.

4. The apparatus of claim 2, wherein the polarizing filter is integrally formed with the spatial filter.

5. The apparatus of claim 4, wherein the first direction is substantially perpendicular to the direction of the first opening, and the second direction is substantially perpendicular to the direction of the second opening.

6. The apparatus of claim 4, wherein the direction of the first opening is substantially perpendicular to the direction of the second opening.

7. The apparatus of claim 1, wherein the light emitter comprises a plurality of lights sources configured to separately emit the straight polarized lights.

8. The apparatus of claim 1, wherein the openings of the spatial filter correspond to the straight polarized lights and the openings of the spatial filter are located at ends of a direction substantially perpendicular to the polarized directions.

9. The apparatus of claim 1, wherein the light detector comprises a plurality of light detectors, the light detectors comprise a dividing member configured to divide the reflected lights into polarized lights, and the light detectors individually detect the polarized lights.

10. The apparatus of claim 9, wherein the light detectors comprise two kinds of the lights detectors, and the polarized lights are substantially perpendicular to each other.

11. The apparatus of claim 9, wherein the dividing member comprises a splitter.

12. The apparatus of claim 9, wherein the dividing member comprises:

a reflecting mirror configured to divide the reflected lights into a plurality of light fluxes; and a plurality of polarizing filters configured to provide the divided light fluxes with different polarized directions.

13. The apparatus of claim 12, wherein the reflecting mirror is configured to divide the reflected lights into the two light fluxes, and the spatial filter is configured to provide the two light fluxes with perpendicular polarized directions.

14. The apparatus of claim 1, further comprising a regular reflection cut filter arranged at a rear optical axis of the optical member to cut regularly reflected lights in the reflected lights.

15. The apparatus of claim 1, further comprising a ½ wavelength plate arranged at any one of an optical axis between the optical member and the spatial filter and a rear optical axis of the condenser lens.

16. A method of detecting a defect of an object, the method comprising:

emitting straight polarized lights having different polarized directions;

partially cutting the straight polarized lights using openings of a spatial filter;

condensing the straight polarized lights passing through the openings on the object; and detecting light reflected from the object;

wherein the spatial filter has a first opening and a second opening therein, wherein a first polarizing portion configured to polarize the straight polarized lights in a first direction is arranged in the first opening, and a second polarizing portion configured to polarize the straight polarized lights in a second direction different from the first direction is arranged in the second opening.

* * * * *